United States Patent [19]

Hallermayer et al.

[11] Patent Number: 4,879,216
[45] Date of Patent: Nov. 7, 1989

[54] SPECIFIC ANTIBODY AGAINST HEART MUSCLE LIGHT CHAINS, A PROCESS FOR THE PREPARATION THEREOF AND A REAGENT CONTAINING IT

[75] Inventors: Klaus Hallermayer, Munich; Siegfrid Looser, Weilheim; Hugo Katus, Bammental, all of Fed. Rep. of Germany

[73] Assignee: Boehringer Mannheim GMBH, Mannheim, Fed. Rep. of Germany

[21] Appl. No.: 165,288

[22] Filed: Mar. 8, 1988

[30] Foreign Application Priority Data

Mar. 11, 1987 [DE] Fed. Rep. of Germany ....... 3707746

[51] Int. Cl.$^4$ .................. G01N 33/577; G01N 33/569
[52] U.S. Cl. ........................................ 435/7; 436/542; 436/548; 436/800; 436/804; 436/811; 436/815; 436/518; 436/531; 435/68; 435/172.2; 435/240.27; 935/110; 530/387; 530/809
[58] Field of Search ............... 436/548, 518, 531, 542, 436/800, 804; 435/172.2, 240.27, 7, 68; 935/110; 530/387, 809

[56] References Cited

PUBLICATIONS

Haber, E. et al., J. Mol. Cell. Cardiol., 14, Suppl. 3, 139–146, (1982).
Shimizu, T. et al., J. Mol. Biol., 183(2), 271–82, (1985).
Chemical Abstracts, I, 98:103675b, (1983).
Chemical Abstracts, II, 103:139193d, (1985).

Primary Examiner—Christine M. Nucker
Attorney, Agent, or Firm—Felfe & Lynch

[57] ABSTRACT

The present invention provides a specific antibody against heart muscle light chains (HMLC) with a cross-reactivity against skeletal muscle light chains (SMLC) of less than 5%. The present invention also provides a process for the preparation of this specific antibody, wherein a mammal is immunized with HMLC I and/or HMLC II and the crude serum is recovered and subjected to an immunosorptive purification on an SMLC immune adsorbent based on silicate. Furthermore, the present invention provides a reagent for the determination of HMLC which contains antibodies against HMLC according to the present invention.

20 Claims, No Drawings

SPECIFIC ANTIBODY AGAINST HEART MUSCLE LIGHT CHAINS, A PROCESS FOR THE PREPARATION THEREOF AND A REAGENT CONTAINING IT

The present invention is concerned with specific antibodies against heart muscle myosin light chains (HMLC), with the preparation thereof and with the use thereof in an immunological reagent for the determination of HMLC.

Myosin is a protein with a molecular weight of about 500,000. It consists of two heavy chains with a molecular weight of about 200,000, two light chains I (HMLC I) with a molecular weight of about 26,000 and two light chains II (HMLC II) with a molecular weight of about 18,000. Myosin is present in the thick filaments of the heart and skeletal muscalature.

Due to heart muscle necroses caused by infarct, HMLC from the breakdown of myosin passes into the blood plasma and thus represents a specific parameter which appears to be suitable not only for the diagnosis and monitoring of a myocardial infarct but which can also give information regarding the extent of the heart muscle damage (see Circulation, 58, 1130/1968; Jap. Cardiol. J., 44, 185/1980; Am. J. Cardiol., 41, 641/1978; Circulation 60 (Suppl. II), 139/1979).

Since the half life time of HMLC in the plasma is, with about 70 to 80 minutes, very short, a later decrease after the infarct event or a broad course of the curve of continuing liberation of HMLC can be assumed. Thus, in contradistinction to the otherwise determined "infarct enzymes" CK, CK-MB, GOT and LDH, a more dependable diagnosis and monitoring is possible with the determination of HMLC. Furthermore, more dependable pronouncements for the assessment of unstable angina pectoris appear to be possible since, in such cases, due to a myocardial infarct possibly present, HMLC are also swept out (Am. J. Cardiol., 54, 964/1894). Since, however, only small amounts of HMLC thereby get into the blood plasma, a sensitive and specific method of determination is necessary. In such cases, immunological methods of determination are usually suitable as methods of detection.

A radioimmunoassay for HMLC has already been described in Am. J. Clin. Path., 71, 309-318/1978. This is a competitive radioimmunoassay in which the HMLC from a sample and iodinated HMLC compete for polyclonal antibodies which are adsorbed on a solid phase. However, a disadvantage of this process is that the cross-reactivity between HMLC and skeletal muscle light chains (SMLC) for the antiserum used is about 6.8%. Admittedly, it has been suggested to purify the antiserum against HMLC by removal of the SMLC antibodies or by fractionation with affinity chromatography but hitherto it has not been possible in this way to make available antibodies against HMLC which show a sufficiently small cross-reactivity with SMLC. Thus, in Jap. Circulation, 44, 185-186/1980, in an immunological sandwich test, a cross-reactivity of 8% was ascertained. In Circulation, 58, 1130-1136/1978, there was reported a cross-reactivity of 2.9 to 10% in an immunological sandwich test. The cross-reactivity of each of the antibodies used in the test was 8.4%. Following standard practice, the value of the cross-reactivity, given as 2.9%, is $(8.4)^{\frac{1}{2}}$.

In Molecular Immunology, 19, 451-455/1982, an attempt was made to overcome this disadvantage in that, instead of polyclonal antibodies, there were used monoclonal antibodies. However, these antibodies also only showed an unsatisfactory cross-reactivity (17%). The monoclonal antibodies described in European patent specification No. 0,205,177 are also not suitable for the specific determination of HMLC. All the antibodies there described, which react with HMLC for patient's serum, also react with SMLC to a considerable extent.

It is an object of the present invention to overcome the above described disadvantages and to make available antibodies against HMLC with only a small cross-reactivity towards SMLC, as well as a process for the preparation of such antibodies.

Thus, according to the present invention, there are provided antibodies against HMLC with a cross-reactivity against SMLC of less than 5, preferably of less than 2% and especially preferably of less than 1%. Such antibodies can be obtained by the process according to the present invention which is described hereinafter.

The present invention thus also provides a process for the preparation of antibodies against HMLC by immunizing an animal species with human HMLC and obtaining the crude serum, wherein the crude serum, possibly after a pre-purification, is purified via a negative immunosorption on an SMLC immune adsorbent based on silicate.

Surprisingly, we have found that, with the process according to the present invention, it is possible to obtain antibodies against HMLC, the cross-reactivity of which against SMLC is less than 5%, preferably less than 2% and especially preferably less than 1%.

The determination of the cross-reactivity takes place with the use of HMLC or of SMLC as solid phase and a maximum of 0.1 μg. of antibody against HMLC per sample. The detection reaction takes place via a conjugate of an antibody directed against the Fcγ part of the HMLC antibody and of a determinable group, for example peroxidase (POD).

HMLC and SMLC can be isolated from heart and skeletal muscle by methods which are well known to the expert and which are described, for example, in Circul. Res., 19, 611/1985 and in Biochem. J., 119, 31/1970. For the immunisation, HMLC I, HMLC II or a mixture of HMLC I and II can be used as immunogen. The immunisation can take place on any desired animal species and according to methods known to the expert.

The crude serum thereby obtained can be used directly for the negative immunosorption on an SMLC immune adsorbent based on silicate.

Preferably, however, there is first carried out a pre-purification step, for example via an ion exchange chromatography or dialysis.

The possibly so pre-treated crude serum is subjected to a negative immunosorption on an SMLC immune adsorbent column based on silicate. For this purpose, the crude serum is applied to a column whereby, surprisingly, those antibodies against HMLC which have a cross-reactivity of less than 5%, preferably of less than 2% and especially preferably of less than 1% are not bound, whereas the antibodies with a higher cross-reactivity are bound. The column is subsequently washed free of protein with the reagents usual for this purpose, for example with phosphate buffer (PBS) (pH 7.5).

The eluate thus obtained can be used directly for the preparation of reagents for an HMLC test. Preferably, however, the eluate is subjected to a further purification, especially by positive immunosorption on an HMLC immune adsorbent.

As carriers for the SMLC immune-adsorbent, there can be used sorbents based on silicate which are known to the expert. The media can be present, for example, as a gel or in pulverised or granulated form. Examples of carriers which can be used include Spherosil ® (manufacturer Rhône-Poulenc), SelectiSper ® (Pierce Eurochemie) and silica gels of J. T. Baker Chem. SMLC is bound covalently to the carrier by conventional processes, possibly via a spacer/linker.

In order to make possible the binding of SMLC to the silicates, these must preferably be provided with bindable groups. For this purpose, the silicates are preferably reacted with reactive silanes, for example trichloroaminopropylsilane or 3-(triethoxysilyl)-propylamine. SMLC can then be coupled directly on to the functional groups which hereby result on the carrier. In an preferred embodiment, on to the functional group is first coupled a bifunctional reagent as spacer and the SMLC subsequently bound thereto. The use of a mixture of SMLC I and SMLC II has thereby proved to be advantageous. The ratio of SMLC I:SMLC II is thereby not critical but there is preferably used a ratio of substantially 1:1 or an excess of SMLC I.

As media, there are especially preferred, for example, silicates which carry aminopropyl, succinoylaminopropyl, hexamethylenediamine, diol, diazafluoroborate, p-nitrophenyl, epoxypropyl, glutaraldehyde and/or glycindoxypropyl groups. Before the coupling, a spacer/linker is possibly introduced on to the carrier material. For this purpose, there can be used the bifunctional linkers which are known to the expert, for example glutardialdehyde, N-succinimidyl 3-(2-pyridyldithio)-propionate, ethyl 4-azidophenyl-1,4-dithiobutyrimidate hydrochloride, 4-fluoro-3-nitrophenyl azide, N-hydroxysuccinimidyl 4-azidobenzoate, m-maleimidobenzoyl N-hydroxysuccinimide ester, N-succinimidyl 6-(4'-azido-2'-nitrophenylamino)-hexanoate, N-succinimidyl (4-iodoacetyl)-aminobenzoate or succinimidyl 4-(p-maleimidophenyl)-butyrate.

It has proved to be advantageous when the distance between the silicate carrier and the SMLC is not more than 20 atoms, a distance of 7 to 12 atoms having proved to be especially advantageous.

It has proved to be especially advantageous when, as silicate, there is used Spherosil which has been activated with trichloroaminopropylsilane or 3-(triethoxysilyl)-propylamine, this aminospherosil then being reacted with glutardialdehyde as bifunctional reagent and the SMLC bound to the carrier so prepared.

It has proved to be advantageous, after purification over the SMLC column, possibly with the introduction of a dialysis step, to follow with a further immunosorptive purification on an HMLC immune adsorbent. As carriers, there can be used those which are known to the expert. However, it is especially advantageous when here, too, there is used an immune-adsorbent based on silicate. For the coupling of HMLC to these carriers, there apply in the same way the remarks made with regard to the SMLC immune adsorbent.

The present invention also provides an immunological reagent for the determination of HMLC with the use of HMLC antibodies with a cross-reactivity of less than 5%, preferably of less than 2% and especially preferably of less than 1% towards SMLC.

With such a reagent, there can be carried out, for example, sandwich tests or competitive tests.

In a sandwich test, there is used an immobilized antibody against HMLC and a conjugate of an HMLC antibody and a determinable group. Either only one or both antibodies to be used can hereby be prepared by the process according to the present invention.

By a determinable group, there is to be understood a group which is known to the expert, for example an enzyme, fluorescent dyestuff or a radio-active labelling.

With such a sandwich test, in the case of incubation times of less than 5 hours, it is still possible to detect HMLC concentrations of 2 ng./ml/ without a cross-reactivity with SMLC being measurable.

The reagent can be present not only as a solution but also on or in a dry reagent carrier. Since a dilution of the sample on a dry reagent carrier is not necessary, shorter incubation times can hereby be achieved.

A preferred embodiment of the reagent contains an antibody against HMLC prepared by the process according to the present invention and immobilised and a conjugate of a monoclonal HMLC antibody and a determinable group. Surprisingly, we have found that a reagent which contains such a combination gives in the test a high sensitivity and a small sample blank value in the case of an HLMC determination.

The preparation of the monoclonal antibody takes place according to the methods known to the expert after immunization with HMLC. The antibodies MAB 4D12 and 1B10 have proved to be especially suitable. The cell lines which correspond to these antibodies have been deposited with the European Collection of Animal Cell Cultures (ECACC) at Porton Down, England, under the deposit numbers ECACC 88022503 (MAB 4D12) and ECACC 88022504 (MAB 1B10).

The present invention also provides a process for the determination of HMLC, wherein a sample is brought together with an antibody against HMLC prepared according to the present invention, which is immobilized, and a conjugate of a monoclonal antibody and a determinable group. The sequence of steps available include "simultaneous", "reverse", and "forward" assays, with different orders of reaction steps. Which format to use is a matter of choice for the investigator. Possibly after an incubation, the solid and liquid phases are separated and the determinable group is determined in one of the two phases.

The following Examples are given for the purpose of ilustrating the present invention, reference thereby being made to the accompanying drawing which shows a calibration curve for an ELISA sandwich test (according to Example 9) with two different MABs, curve 1 being for MAB 4D12 and curve 2 being for MAB 1B10.

EXAMPLE 1.

Preparation and isolation of the myosin light chains (HMLC and SMLC).

HMLC and SMLC were isolated from human skeletal and heart muscle tissue according to the processes described in Circul. Res., 19, 611/1965, and Biochem. J., 119, 31/1970.

EXAMPLE 2.

Obtaining of the antisera.

A mixture of HMLC I (M.W. 26,000) and HMLC II (M.W. 18,000) obtained according to example 1 was used a immunogen. Sheep were first immunized with 55 μl. of a solution of 0.1 mg./ml of HMLC I and II in complete Freund's adjuvant (CFA). Further immunizations took place on the 7th, 14th and 30th day. Thereafter, immunization was carried out every 30 days. In the case of these subsequent injections, in each case there was used 28 μl of an HMLC solution of 0.05 mg./ml. in CFA. After 6 months, the crude serum was obtained.

EXAMPLE 3.

Isolation of polyclonal sheep IgG antibodies against HMLC (PAB{HMLC}S-IgG) from crude serum.

1 liter of crude serum was mixed with 15 g. of Aerosil (manufacturer Degussa), stirred for 1 hour at ambient temperature and centrifuged. Subsequently, the supernatant was mixed with 1.7 mole/liter ammonium sulphate and slowly stirred for 2 hours at ambient temperature. The precipitate was thereafter centrifuged off and homogenized in 0.2 liters of dialysis buffer (15 mMole/liter potassium phosphate and 50 mMole/liter sodium chloride; pH 7.0) and dialysed four times at 4° C. against 10 liters of dialysis buffer. After again centrifuging, the dialysed γ-globulin was purified over DE52-cellulose, eluting with dialysis buffer.

The cross-reactivity of the so purified PAB {HMLC} towards SMLC was up to 100% (determination according to Example 6).

EXAMPLE 4.

Negative immune adsorption of PAB {HMLC} on SMLC immune adsorbent.

PAB {HMLC} solution purified according to Example 3 was made up ad 50 mMole/liter potassium phosphate (pH 7.5), 150 mMole/liter dosium chloride (PBS) and 0.1% azide and, with a concentration of about 15 mg./ml., applied at ambient temperature to an SMLC immune adsorbent column (preparation see Example 8) and washed free of protein with PBS/0.1% azide (PBS: phosphate buffered saline).

EXAMPLE 5.

Positive immunosorption of PAB {HMLC} on HMLC immune adsorbent.

The eluate obtained according to Example 4 was applied, under the conditions described in Example 4, to an HMLC immune adsorbent (preparation analogous to Example 8). After washing with PBS/0.1% azide, it was eluted with 1 mole/liter propionic acid at ambient temperature.

The eluate was subsequently dialysed for 2 hours at 4° C. against deionized water and thereafter at 4° C. overnight against 1 mMole/liter carbonate/bicarbonate buffer (pH 9.5).

EXAMPLE 6.

Determination of the cross-reactivity.

For the determination of the cross-reactivity, there was used a test system consisting of immobilised HMLC and a polyclonal antibody against sheep Fcγ ({sheep-Fcγ}-PAB), conjugated to POD.

(a) Preparation of the solid phase.

As carriers, there were used microtitre plates, manufact. Costar (PVC). Per cavity, there was introduced 0.1 ml. of a solution of 5 μg./ml HMLC and SMLC, respectively in 0.2 mole/liter carbonate buffer (pH 9.4) and incubated overnight at 4° C. After washing twice with PBS, per cavity there was introduced 0.2 ml. of 50 mMole/liter phosphate buffer (pH 7.4), which contained 1% BSA and 0.9% sodium chloride, and incubated for 1 hour at ambient temperature.

(b) Preparation of the POD conjugate.

A polyclonal antibody from rabbits against Fcγ (IgG) ({sheep-Fcγ}-PAB) was coupled with horseradish POD (peroxidase) according to the method described in Meth. in Enzymology, 70, 104–142/1980.

(c) Carrying out of the determination.

The sample was diluted with 50 mMole/liter phosphate buffer (pH 7.4) to 1.0 μg./ml. PAB {HMLC} according to Example 3 and 4 or 0.2 μg./ml. PAB <HMLC> according to Example 5. 0.1 ml. of the so prepared sample was introduced into each cavity and incubated for 1 hour at ambient temperature. After washing twice with PBS, per cavity there was introduced 0.1 ml. of <sheep-Fcγ> PAB-POD conjugate (POD activity 0.2 U/ml.) and incubated for 1 hour at ambient temperature.

After washing twice with PBS, per cavity there was introduced 0.1 ml. ABTS ® (2,2'-azino-di-(3-ethylbenzthiazoline-6-sulphonic acid diammonium salt (1.9 mMole/liter in 100 mMole/liter phosphate/citrate buffer (pH 4.4), 3.2 mMole/liter sodium perborate). After an incubation period of 45 minutes, the extinction difference was determined against the blank at 405 nm. The cross-reactivity was determined from the extinction values which were obtained for the same sample with an HMLC- and an SMLC-coated solid phase. It was hereby found that, after negative immunosorption on SMLC and positive immunosorption on HMLC, no cross-reactivity was detectable of the PAB<HMLC> towards SMLC (see the following Table 1).

TABLE 1

| sample | extinction difference ΔE | | cross-reactivity % |
|---|---|---|---|
| | HMLC solid phase | SMLC solid phase | |
| PAB according to Example 3 | 0.752 | 0.500 | 66 |
| PAB according to Example 4 (IS on SMLC column) | 0.440 | 0.008 | 1.8 |
| PAB according to Example 5 (IS on SMLC and HMLC column) | 0.852 | 0.0 | 0 |

IS = immunosorption

EXAMPLE 7.

HMLC determination via an ELISA sandwich test.

For the determination, there was used a test system which consisted of an immobilised <HMLC> PAB (prepared according to Example 5) and a conjugate of an <HMLC>-PAB and POD (conjugated preparation analogous to Example 6b).

(a) Solid phase:
PVC microtitre plates, Costar (b) Coating (immobilisation of <HMLC>-PAB)-0.1 ml/cavity 5 μg./ml. <HMLC>-PAB (Example 5) in 0.1 mole/liter citrate buffer (pH 4.0) incubated overnight at 4° C. and washed twice with PBS (phosphate buffered saline)

(c) After-loading
0.2 ml./cavity with incubation buffer (IB): (50 mMole/liter phosphate buffer (pH 7.4), 0.9% sodium chloride, 1% bovine serum albumin (BSA), wash twice with PBS.

(d) Carrying out of the test 0.1 ml/cavity sample (0–100 ng./ml. HMLC or SMLC added in IB and incubated for 2 hours at ambient temperature and washed twice with PBS.

0.1 ml./cavity add conjugate of <HMLC>-PAB (Example 5) and POD (preparation analogous to Example 6 b) (activity 0.1 U/ml.) in IB and incubate for 2 hours at ambient temperature. Wash twice with PBS.

0.1 ml./cavity substrate solution (ABTS ®, 1.9 mMole/liter in 0.1 mole/liter citrate buffer (pH 4.4), 3.2 mMole/liter sodium perborate) incubate for 45 minutes at ambient temperature.

Wavelength measurement at 405/490 nm on an ELISA reader.

The results obtained are given in the following Table 2:

TABLE 2

| concentration ng./ml. | HMLC E | SMLC E |
| --- | --- | --- |
| 0 | 0.000 | 0.000 |
| 10 | 0.091 | 0.000 |
| 25 | 0.288 | 0.000 |
| 50 | 0.339 | 0.000 |
| 100 | 0.913 | 0.000 |

EXAMPLE 8.

Preparation of the SMLC immune adsorber.

Spherosil (Rhone-Poulenc, XOC 005) washed with 15% nitric acid and water was, after drying, reacted with 10% v/v 3-triethoxysilyl)-propylamine in dimethyl sulphoxide at 85° C. overnight to give Spherosil-NH$_2$. After the reaction, free reagent was washed out with dimethyl sulphoxide and isopropanol and the adsorbent dried at 50° C. Spherosil-NH$_2$ was mixed with 10% glutardialdehyde solution (pH 3.7) and heated for 2 hours to 55° C. The suspension was subsequently filtered off with suction under a vacuum over a glass filter. It was then washed with distilled water in a volume seven times that of the Spherosil volume and with a fivefold volume of 10 mMole/liter potassium phosphate (pH 8.0)/0.1 mole/liter sodium chloride solution.

10 mg. SMLC were added per ml. of Spherosil in 10 mMole/liter potassium phosphate (pH 8.0)/0.1 mole/liter sodium chloride in about 50% of the Spherosil volume used in a round-bottomed flask. The flask was rotated overnight at ambient temperature on a rotary evaporator.

After filtration, the Spherosil was after-washed several times with 0.9% sodium chloride solution, as well as with ethanolamine solution. Subsequently, 3 parts by volume of ethanolamine solution were added thereto and incubated for 1 hour at ambient temperature. After filtering again, it was again washed with sodium chloride solution.

Subsequently, the immune adsorber was adjusted to pH 7.5 with PBS and equilibrated with PBS/sodium azide. Storage took place at 4° C.

EXAMPLE 9.

HMLC determination via an ELISA sandwich test with monoclonal antibody.

For the determination, a test system was used which consisted of an immobilised <HMLC>-PAB (prepared according to Example 5) and a conjugate of an <HMLC>-MAB (4D12 or 1B10) and POD (Conjugate preparation analogous to Example 6 b).

Solid phase, coating, after-loading and carrying out of the determination were analogous to Example 7. The results obtained can be seen from the Figure of the accompanying drawing. The curves show that, in the case of small sample blank values, a high sensitivity can be achieved.

We claim:

1. Substantially pure antibody which specifically binds to heart muscle myosin light chain and which has a cross reactivity of less than 5% against skeletal muscle myosin light chain.

2. Antibody of claim 1, wherein said antibody has a cross reactivity of less than 2% against skeletal muscle myosin light chain.

3. Antibody of claim 1, wherein said antibody has a cross reactivity of less than 1% against skeletal muscle myosin light chain.

4. Antibody of claim 1, obtained by immunizing a subject mammal with an immunogen comprising at least one of heart muscle myosin light chain I and heart muscle myosin light chain II to provoke production of antibody by said mammal, recovering antibody containing serum therefrom, and immunosorptively removing said antibody from said serum by contacting said serum with a silicate based immunoadsorbent carrier containing skeletal muscle myosin light chain.

5. Process for obtaining a substantially pure antibody which specifically binds to heart muscle molecular light chain and has cross reactivity of less than 5% with skeletal muscle myosin light chain, comprising immunizing a subject mammal with an immunogen comprising at least one of heart muscle myosin light chain I and heart muscle myosin light chain II to provoke production of antibody by said mammal, recovering antibody containing serum therefrom, and immunosorptively removing said antibody from said serum by contacting said serum with a silicate based immunosorbent carrier containing skeletal muscle myosin light chain.

6. Process of claim 5, wherein said carrier is a gel.

7. Process of claim 5 or 6, wherein said skeletal muscle myosin light chain is coupled to said carrier by a bifunctional linker.

8. Process of claim 7, wherein said bifunctional linker is glutardialdehyde and said carrier is activated by amino groups.

9. Process of claim 7, wherein said skeletal muscle myosin light chain is bound to said carrier at a distance of no more than twenty atoms.

10. Monoclonal antibody which specifically binds to heart muscle myosin light chain and has cross reactivity of less than 5% against skeletal muscle myosin light chain.

11. Monoclonal antibody of claim 10, selected from the group consisting of monoclonal antibody produced by hybridoma cell line 4D12 (ECACC 88022503) and hybridoma cell line 1B10 (ECACC 88022504).

12. Hybridoma cell line which produces monoclonal antibody which specifically binds to heart muscle myosin light chain and has cross reactivity with skeletal muscle myosin light chain of less than 5%.

13. Hybridoma cell line of claim 12, selected from the group consisting of 4D12 (ECACC 88022503) and 1B10 (ECACC 88022504).

14. Monoclonal antibody of claim 10, wherein said monoclonal antibody is conjugated to a determinable group.

15. Reagent for determining heart muscle myosin light chain comprising an antibody which specifically binds to heart muscle myosin light chain and has cross reactivity of less than 5% with skeletal muscle myosin light chain immobilized to a solid carrier.

16. Reagent of claim 15, further comprising a second antibody which carries a determinable group and which specifically binds to heart muscle myosin light chain.

17. Reagent of claim 15, wherein said antibody is a monoclonal antibody.

18. Reagent of claim 17, wherein said monoclonal antibody is produced by cell line 4D12 (ECACC 88022503) or cell line 1B10 (ECACC 88022504).

19. Method for determining heart muscle myosin light chain in a sample comprising contacting said sample with an immobilized antibody which specifically binds to heart muscle myosin light chain and has a cross reactivity of less than 5% against skeletal muscle myosin light chain and a monoclonal antibody which carries a determinable group and which specifically binds to heart muscle myosin light chain and has a cross reactivity of less than 5% against skeletal muscle myosin light chain, forming complexes between said antibodies and heart muscle myosin light chain and determining said determinable group in light or immobilized phase an indication of heart muscle myosin light chain.

20. Method of claim 19, wherein said monoclonal antibody is selected from the group consisting of monoclonal antibody produced by hybridoma cell line 4D12 (ECACC 88022503) and 1B10 (ECACC 88022504).

* * * * *

UNITED STATES PATENT AND TRADEMARK OFFICE
CERTIFICATE OF CORRECTION

PATENT NO.  : 4,879,216

DATED       : November 7, 1989

INVENTOR(S) : Klaus Hallermayer, et al.

It is certified that error appears in the above-identified patent and that said Letters Patent is hereby corrected as shown below:

Column 6, line 9:   change "0.2" to -- 0.1 --.

Column 8, line 28:  change "molecular" to -- myosin --.

Signed and Sealed this

Twenty-fifth Day of December, 1990

Attest:

HARRY F. MANBECK, JR.

Attesting Officer

Commissioner of Patents and Trademarks